United States Patent [19]

Sönksen et al.

[11] Patent Number: 5,426,096
[45] Date of Patent: Jun. 20, 1995

[54] USE OF HUMAN GROWTH HORMONE

[76] Inventors: Peter Sönksen, Department of Endocrinology & Chemical Pathology UMDS, St. Thomas Hospital, London, SE1 7EH, Great Britain; Miroslav Würzburger, Department of Endocrinology "Zvezdara", University Medical Centre, D. Tucovica 161, 11 000 Beograd, Yugoslavia

[21] Appl. No.: 853,388

[22] Filed: Mar. 18, 1992

[51] Int. Cl.$^6$ .............. C07K 14/62; C07K 14/61; A61K 38/28; A61K 38/27
[52] U.S. Cl. ............................... 514/12; 514/3; 530/303; 530/324
[58] Field of Search ............ 514/12, 3; 530/303, 530/324

[56] References Cited

U.S. PATENT DOCUMENTS 4,857,506 8/1989 Tyle ............................. 514/12

FOREIGN PATENT DOCUMENTS

WO8900166 1/1989 WIPO .

OTHER PUBLICATIONS

Wurzburger, et al., Restoration of hypoclycaemia awareness by human recombinant growth hormone, The Lancet, vol. 339 (1992) pp. 496–497.

Holly, et al., The role of growth hormone in diabetes mellitus, J. Endocrinol, vol. 118 (1988) pp. 353–364.
Lager, I., The insulin-antagonistic effect of the counter-regulatory hormones, J. Intern. Med. Suppl., vol. 735 (1991) pp. 41–47.
Fowelin, et al., Characterization of the insulin-antagonistic effect of growth hormone in man, Diabetologia, vol. 34, No. 7 (1991), pp. 500–506.
Fowelin, et al., Postprandial hyperglycaemia following a morning hypoglycaemia in type 1 diabetes mellitus, Diabetic Med., vol. 7, No. 2 (1990), pp. 156–161.
Rizza, R. et al "Role of Glycagon, Catediolamines, and Growth Hormone in Human Glucose, Counteregulation", J. Clin Invest vol. 64, pp. 62–71 (1979).

*Primary Examiner*—Howard E. Schain
*Assistant Examiner*—Lynn Touzeau
*Attorney, Agent, or Firm*—Pollock, Vande Sande & Priddy

[57] ABSTRACT

The invention relates to the use of human growth hormone, or any functional analogue therof, for the manufacture of a medicament for the treatment or prophylaxis of hypoglycemic unawareness in diabetes mellitus. Preferably the human growth hormone, or any functional analogue thereof, is administered repeatedly, which could be daily. The daily dose is between 1–10 IU and could be given at a dose of 4 IU daily during one week. The invention also relates to a method for treatment and prophylaxis of hypoglycemic unawareness by administration of human growth hormone, or any funtional analogue thereof.

9 Claims, No Drawings

USE OF HUMAN GROWTH HORMONE

TECHNICAL FIELD

This invention relates to a new medical effect of human growth hormone (hGH) for the treatment and prophylaxis of hypoglycaemia unawareness in long-standing insulin-dependent diabetes mellitus.

BACKGROUND ART

Human growth hormone is a protein consisting of a single chain of 191 amino acids. The molecule is cross-linked by two disulphide bridges and the monomeric form has a molecular weight of 22 kDa. However, pituitary human growth hormone is not homogeneous. For example, a smaller 20 kDa hGH variant produced from the same gene is also known. The "basic hGH" variant (hGH-V) expressed by the placenta during pregnancy is another analogue which is a product of a separate gene. Like the 22 kDa hGH it consists of 191 amino acids but in various positions throughout the molecule 13 of them are different.

Recombinant hGH (22 kDa) has been available commercially for several years. It is preferred over the pituitary derived products because the product prepared from human tissue might be contaminated and transmit infections. Of particular concern is the slow virus disease, Creutzfeld-Jacob's disease. Two types of therapeutically useful recombinant hGH preparations are present on the market: the authentic one, e.g. Genotropin ®, Kabi Pharmacia AB, and an analogue with an additional methionine residue at the N-terminal end, e.g. Somatonorm ®.

By growth hormone (hGH) is here meant any of the above mentioned variants or any functional analogue with human growth hormone activity.

Diabetes mellitus is a chronic syndrome of impaired carbohydrate, protein and fat metabolism secondary to insufficient secretion of insulin or to target tissue insulin resistance. Diabetes mellitus is normally called diabetes. It occurs in two major forms: insulin-dependent diabetes mellitus (type I) and non-insulin-dependent diabetes mellitus (type II).

Hypoglycaemia is an abnormally diminished concentration of glucose in the blood, which may lead to tremor, sweating, piloreaction, hypothermia and ultimately convulsions and coma. This is a dangerous condition for a diabetic patient, especially if it occurs during the night and the patient does not wake up.

Normally, hypoglycaemia leads to an increase in counterregulatory hormones such as catecholamines, cortisol and glucagon.

Hypoglycaemia can occur at any time in an insulin-treated diabetic subject, and is then, when the patient notices the signals, normally treated with carbohydrate intake or administration of glucose to the patient.

Hypoglycemic unawareness is a serious and still unsolved clinical problem in some insulin-dependent diabetic patients. These patients lack the normal warning symptoms of a hypoglycemic episode. Moreover, hypoglycemic unawareness is often associated with inadequate glucose counterregulation during hypoglycaemia. Reference is made to Ryder R. E. J., et al., Brit J Med, 301 (1990) 783–787 and White N. H., et al., N Engl J Med, 308 (1983) 485–491.

We have now surprisingly found that hypoglycemic awareness was restored in a group of diabetic patients during hGH treatment and that the restored awareness lasted for a year or more after completion of the trial.

The necessary dose of growth hormone to provide this effect is estimated to be 1–10 IU given daily and then repeated for at least one week, but can of course go on continuously if needed.

In the study, as reported below, 4 IU of hGH was given every day during one week.

The invention relates to the use of human growth hormone, or any functional analogue therof, for the manufacture of a medicament for the treatment or prophylaxis of hypoglycemic unawareness in diabetes mellitus.

Preferably the human growth hormone, or any functional analogue thereof, is administered repeatedly, which could be daily. The daily dose is between 1–10 IU and could be given at a dose of 4 IU daily during one week.

The invention also relates to a method for treatment and prophylaxis of hypoglycemic unawareness by administration of human growth hormone, or any functional analogue thereof. Preferably the human growth hormone, or functional analogue thereof, is administered daily and given at a dose of 4 IU daily during one week.

Studies

Four persons who had had insulin-dependent diabetes mellitus (IDDM) for at least three years were included in the study. They were all C-peptide negative (without endogenous beta cell activity) and had suffered from hypoglycemic unawareness for 6 months to 2 years before they entered the study. Therapy with rhGH Genotropin ® (Kabi Pharmacia, Sweden) was given in hospital for 7 consecutive days by subcutaneous injections of 4 IU at 8 pm every day.

In all four patients hypoglycemic awareness was restored by Genotropin treatment and the awareness has lasted for more than a year after treatment.

Patient 1. Female; 45 years of age; duration of IDDM 14 years. On insulin treatment from the start of the disease. She was unable to recognize any hypoglycaemic symptoms for 18 months before she entered the rhGH study. She reported 3 to 4 hypoglycaemic comas per month which occurred between 2 and 4 am and were noticed by her family as a sudden appearance of deep and strenuous breathing and unusual movements of her arms and legs. During the episodes it was impossible to wake her up until intravenous administration of hypertonic glucose had been given which promptly resulted in disappearance of the symptoms. The hypoglycaemic coma rarely occurred during daily activities and presented with sudden loss of consciousness without any prior hypoglycaemic symptom. After short-term rhGH treatment she reported complete recovery of awareness of hypoglycaemic symptoms which so far has lasted for 18 months.

Patient 2. Male; 21 years of age; duration of IDDM 15 years. His parents reported 2 to 3 hypoglycaemic episodes per month which regularly occurred during the night. Every time they noticed unusually deep breathing and after trying to wake him up they realized that he was unable to communicate. After administration of sugar the patient slowly returned to consciousness, but was unaware of previous events. After rhGH treatment his awareness of hypoglycaemia was restored for one year. Hypoglycaemic episodes are rare now, but when they occur he wakes up during the night feeling hunger and sweating.

Patient 3. Male; 29 years of age; duration of IDDM 17 years. The family reported 2 to 3 hypoglycaemic episodes per month, usually during the night. They were alerted by the patient grinding his teeth and when they tried to wake him up, he was incoherent, unable of moving. After sugar administration recovery of consciousness was slow and the patient could not recall any details of the event. After rhGH treatment his awareness of hypoglycaemia was normalized.

Patient 4. Male; 49 years of age; duration of IDDM 15 years. The family reported 6 to 8 episodes for the last six months before he entered the study. The hypoglycaemic episodes occurred mainly during the night when they presented with coma or in the early morning when the patient awoke spontaneously but sat in bed unable to communicate. The latter type of hypoglycaemic episode was also recorded by the medical staff during hospitalisation when blood glucose levels were found to be between 1.6 and 1.9 mmol/L.

After intravenous glucose administration the patient became conscious but could not recall any detail of the event. Clinical examination revealed hypertrophic lipodiustrophy on the abdominal wall where he selfinjected monocomponent insulin. Complete recovery of hypoglycemic awareness was noticed after rhGH treatment.

Surprisingly, the restored and long-lasting hypoglycemic awareness in all the patients treated is the consequence of one week of rhGH treatment.

Thus, hGH treatment is an important tool for helping patients suffering from hypoglycemic awareness and or may be even more importantly, prophylactically for those who are at risk for developing it.

We claim:

1. Method for treatment of hypoglycemic unawareness by administration of an effective amount of human growth hormone to a diabetes mellitus patient having hypoglycemic unawareness and being in need of said treatment.

2. Method according to claim 1, in which the human growth hormone is administered repeatedly.

3. Method according to claim 2, in which the human growth hormone is administered daily.

4. Method according to any of claims 1, in which the human growth hormone is administered daily in a dose 1-10 IU.

5. Method according to claim 4, in which the human growth hormone is administered at a dose of 4 IU daily during one week.

6. Method according to claim 2, in which the human growth hormone is administered daily in a dose 1-10 IU.

7. Method according to claim 6, in which the human growth hormone is administered at a dose of 4 IU daily during one week.

8. Method according to claim 3, in which the human growth hormone is administered daily in a dose 1-10 IU.

9. Method according to claim 8, in which the human growth hormone is administered at a dose of 4 IU daily during one week.

* * * * *